(12) United States Patent
Zhang et al.

(10) Patent No.: US 6,490,478 B1
(45) Date of Patent: Dec. 3, 2002

(54) SYSTEM AND METHOD FOR COMPLEXITY ANALYSIS-BASED CARDIAC TACHYARRHYTHMIA DETECTION

(75) Inventors: Xu-Sheng Zhang, Santa Ana Heights, CA (US); Dongping Lin, Irvine, CA (US)

(73) Assignee: Cardiac Science Inc., Irvine, CA (US)

( * ) Notice: Subject to any disclaimer, the term of this patent is extended or adjusted under 35 U.S.C. 154(b) by 0 days.

(21) Appl. No.: 09/669,020

(22) Filed: Sep. 25, 2000

(51) Int. Cl.$^7$ .......................................... A61B 5/0464
(52) U.S. Cl. .......................................... 600/518; 607/4
(58) Field of Search .................... 607/4, 5, 14; 600/515, 600/518, 517

(56) References Cited

U.S. PATENT DOCUMENTS 5,342,402 A * 8/1994 Olson et al. .................... 607/5
5,545,186 A * 8/1996 Olson et al. .................. 607/14

* cited by examiner

*Primary Examiner*—George R. Evanisko
(74) *Attorney, Agent, or Firm*—Gottlieb, Rackman & Reisman, P.C.

(57) ABSTRACT

A system and method based on electrocardiogram (ECG) complexity analysis for real-time detecting shockable ventricular fibrillation (VF) and ventricular tachycardia (VT), and discriminating them from non-shockable tachyarrhythmia (e.g. supraventricular tachycardia (SVT) and atrial fibrillation (AF)) and high-frequency noise. In the disclosed invention, complexity measure CM (0 to 100), quantitatively characterizing the complexity nature of the non-linear dynamics underlying cardiac arrhythmia, is extracted from the sensed patient ECG signal using ECG complexity analysis. From the calculated complexity measure, by three thresholds (low complexity threshold (LCT), mediate complexity threshold (MCT), and high complexity threshold (HCT)), different kinds of tachyarrhythmia (i.e. heart rate (HR) above a preset rate threshold) and high-frequency noise are discriminated from each other: for non-shockable tachyarrhythmia, $CM \leq LCT$; for VT, $LCT < CM \leq MCT$; for VF, $MCT < CM \leq HCT$; and for high-frequency noise, $HCT < CM$. The disclosed system and method can be used as a primary cardiac tachyarrhythmia detection scheme or as a backup system to reconfirm arrhythmia detection using conventional techniques.

31 Claims, 9 Drawing Sheets

SYSTEM AND METHOD FOR COMPLEXITY ANALYSIS-BASED CARDIAC TACHYARRHYTHMIA DETECTION

BACKGROUND OF THE INVENTION

A. Field of The Invention

The present invention relates generally to a new cardiac tachyarrhythmia detection system and method, which is suitable for use in cardiac therapy and monitoring equipment and other similar devices which incorporate techniques of ECG processing and analysis. These devices may include out-of-hospital or in-hospital, external automatic defibrillator (AED), implantable cardioverter defibrillator (ICD), pacemakers, and other similar systems. More particularly, the present invention relates to a system and method capable of discriminating ventricular fibrillation (VF), ventricular tachycardia (VT), non-shockable tachyarrhythmia, and high-frequency noise, using an ECG complexity measure CM.

B. Description of The Prior Art

Despite major advances in the diagnosis and treatment of heart disease over the past decades, a substantial number (350,000 in the USA) of patients each year suffer sudden cardiac arrest (SCA) due to, for example, ventricular tachycardia (VT) or ventricular fibrillation (VF). However, the national survival rate of SCA is merely about 5%. The standard therapy for SCA is early cardioversion/defibrillation either by implantable cardioverter defibrillators (ICD) or by automatic external defibrillator (AED). An important parameter that affects the reliability and accuracy of these therapies is the algorithm or technique used to detect shockable VT and VF and while avoiding unnecessary shocks possibly caused by non-shockable tachyarrhythmias (e.g. supraventricular tachycardia (SVT), atrial fibrillation (AF), etc.) and some high-frequency noise commonly encountered under practical situations.

Since electrical shocks always have adverse affects on the myocardium, another primary goal of all cardiac therapies is to minimize the number and energy level of electrical signals delivered to the patient. To this end, VT, which requires much lower energy levels for effective therapy, must be effectively differentiated from VF. Moreover, the safety of a device, as well as its ease of use, extent of automatic operation, and widespread acceptance also depend on the performance of the arrhythmia detection system and method.

All devices and systems monitoring the cardiac state of a patient and/or generating antitachyarrhythmia therapy rely on the analysis of the electrocardiogram (ECG) from the patient. The analyses proposed and used so far were based on manipulation of information in the time-domain, frequency-domain, time-frequency domain, and bispectral domain, and even nonlinear dynamics domain. However, all these manipulations have fundamental limitations associated with the linear nature, computational complexity, or difficulty in real-time implementation as well as low sensitivity and specificity. For this reason, currently, the percentage of patients with ICDs who are paced or shocked unnecessarily exceeds 40%. Similarly, AEDs are only 90% effective or sufficiently sensitive to detecting ventricular tachyarrhythmia and 90–95% accurate in detecting and correctly classifying other heart rhythms. Moreover, discrimination of VT from VF is still a difficult object to achieve using existing algorithms for ICD and AED. Therefore, a need still exists for a simple and effective arrhythmia detection system and method using sophisticated signal processing techniques.

It has been found that the electrical activity of the heart is best described as by a non-linear dynamical system. The theory used to describe such systems is known as non-linear dynamics theory, which can be used therefore to analyze the dynamic mechanisms underlying the cardiac activities. Dynamical systems such as the heart can exhibit both periodic and chaotic behaviors depending on certain system parameters. For instance, VF is a highly complex, seemingly random phenomenon, and can be described as chaotic cardiac behavior. Therefore, a diagnostic system with the ability to quantify abnormalities of a non-linear dynamic cardiac system would be expected to have an enhanced performance. In fact, methods have been described which were derived from nonlinear dynamics in ECG signal processing and arrhythmia prediction and detection. For example, Poincare map or return map of the ECG amplitude for cardiac fibrillation detection was disclosed in U.S. Pat. No. 5,439,004, issued to Duong-Van. U.S. Pat. No. 5,643,325, issued to Karagueuzian et al., disclosed the degree of deterministic chaos in phase-plane plot may indicate a propensity for fibrillation including both the risk of fibrillation and the actual onset of fibrillation. A method for detecting a heart disorder using correlation dimension (by Grassberger-Procaccia algorithm) was also disclosed in U.S. Pat. No. 5,643,325, incorporated herein by reference. A slope filtered point-wise correlation dimension algorithm is utilized to predict imminent fibrillation, as disclosed in U. S. Pat. No. 5,425,749, issued to Adams, and "Slope Filtered Pointwise Correlation Dimension Algorithm and Evaluation with Prefibrillation Heart Rate Data," were disclosed in the *Journal of Electrocardiology*, Vol. 24, Supplement, pp. 97–101, authored by Kroll and Fulton. These non-linear dynamics derived methods are based on the phase space reconstruction, and the computational demand and complexity are considerable for current ICD and AED, therefore, they are still difficult to apply in the real world.

The cardiac electrical signal is the complex resultant of a plurality of spatial and temporal inputs and many non-linear dynamic features or characteristics should be expected in this signal, such as different spatio-temporal patterns manifested in the ECG. One such dynamic feature is 'complexity.' Different non-linear dynamic cardiac behavior is associated with different degrees of complexity. Therefore, the measure characterizing complexity can be used as an effective tool for detecting VT and VF. Correlation dimension and approximate entropy have been proposed as means of characterizing complexity, however, these approaches requires highly accurate calculations involving long data segments and are very time-consuming (See Caswell Schuckers S. A., "Approximate Entropy as a Measure of Morphologic Variability for Ventricular Tachycardia and Fibrillation", *Computers in Cardiology*, 1998, 25:265–268). Hence, these approaches cannot be extended to real-time application in ICD and AED. Another method of complexity analysis was proposed by Lempel and Ziv in "On the Complexity of Finite Sequences", *IEEE Trans. Information Theory*, 1976, IT-22: 75–81. Zhang et al. have disclosed some results of this kind of complexity analysis for normal sinus rhythm, VT, and VF, in "Detecting Ventricular Tachycardia and Fibrillation by Complexity Measure", *IEEE Transactions on Biomedical Engineering*, 1999, 46: 548–555. All the above-mentioned references are incorporated herein by reference. However, none of these references mention the way to perform real-time complexity analysis in ICDs and AEDs. Moreover, none of these references discuss a method that can be used to avoid unnecessary therapy caused by SVT or high-frequency noise.

In view of the clinical importance of ventricular conditions, more emphasis should be put on the analysis and feature extraction of the ventricular electrical activity, manifested as QRS complex on the ECG. By an optimized threshold method, the "complexity" of ventricular activity patterns can be analyzed quantitatively by complexity analysis after transforming it into a character sequence. The cardiac tachyarrhythmia detection system and method of present invention as disclosed herein is simple, computationally efficient, effective, robust and reliable, and well suited for real-time implementation and, at the same time, it has immunity ability to noise and artifacts. Therefore, it offers all the desirable features for the practical application in AED and ICD.

OBJECTIVES AND SUMMARY OF THE INVENTION

The present invention fulfills the need in AEDs and ICDs by providing a cardiac arrhythmia detection system and method, which provides a clearer and more reliable indication of the onset of VT and VF that has been available in the prior arts and, at the same time, avoids possible misidentifications caused by SVT, high-frequency artifacts or noise.

It is, accordingly, an objective of the present invention to provide an improved system and method for simultaneously detecting shockable VT and VF, and discriminating non-shockable SVT, and high-frequency artifacts and noise as well.

A further object of the present invention is to provide such a detection system and method which is capable of correctly and accurately distinguishing in real time different kinds of cardiac episodes (shockable and non-shockable) using an easy-to-implement algorithm without computation complexity.

It is an additional object of the present invention to utilize the dynamical non-linear nature of the heart as exhibited in ECG signals to detect VT and VF by quantitative measurements thereof using non-linear dynamic theory.

It is still another further object of the present invention to provide such a detection system and method, which discriminates VT from VF and thereby allows the application of lower-energy cardioversion therapy for VT to provide significant energy savings for the battery powered device and improved patient comfort, such as an implantable cardioverter/defibrillator, high-energy defibrillation therapy for VF and, at the same time, avoiding unnecessary shock for SVT.

These and other objects of the invention are realized by providing a novel cardiac tachyarrhythmia detection system and method as described in more detail below. More specifically, the present invention pertains to a method and apparatus which uses the complexity measure of a nonlinear dynamical system associated with cardiac rhythms to detect VT, VF, SVT and high-frequency noise.

As discussed above, the non-linear dynamic cardiac activity has different characteristics for different cardiac rhythms. These characteristics are apparent from the different spatio-temporal patterns in the corresponding ECG waveforms with different complexity. In accordance with this invention, the complexity of these patterns is quantified and designated as a complexity measure CM. The CM, calculated by a complexity analysis, has a value between 0 to 100. The larger CM value, the more complex the activity. For non-shockable tachyarrhythmias (such as SVT and atrial fibrillation (AF)), the corresponding CM is lower than for VT and VF since, during SVT and AF, the cardiac activity has a regular, more organized, and periodic state. CM has a lower value for VT than for VF, since cardiac activity during VT is more stable and the ventricular activity (QRS complexes) basically looks more similar than that of VF. The high-frequency artifacts or noise manifest random-like activity, therefore, the corresponding CM values are much higher than the values for cardiac activities.

By directly analyzing the non-linear dynamics representing cardiac activities and quantitatively characterizing the associated complexity as a parameter CM, the detection system and method of the present invention is able to overcome the limitations of existing methods and is capable of discriminating accurately between VT, VF, SVT, and high-frequency noise.

This invention offers a considerable improvement over current methods of analysis by employing a new criterion for reliable separation among VT, VF, SVT, and high-frequency noise. Particularly, by using three CM thresholds (i.e. low complexity threshold (LCT), mediate complexity threshold (MCT), and high complexity threshold (HCT)), different kinds of tachyarrhythmia (i.e. heart rate (HR) above a pre-set rate threshold) and high-frequency noise are discriminated from each other: for non-shockable tachyarrhythmia, $CM \leq LCT$; for VT, $LCT < CM \leq MCT$; for VF, $MCT < CM \leq HCT$; and for high-frequency noise, $HCT < CM$. In this way, the arrhythmia is determined accurately and rapidly allowing the device or system to select the corresponding therapy, if required.

Moreover, since VT, VF, SVT, and high-frequency noise are accurately detected in appropriate shock treatment and lower energy consumption is achieved.

BRIEF DESCRIPTION OF THE DRAWINGS

The above and other objects and advantages of the present invention will be more fully understood with reference to the following detailed description, taken in conjunction with the accompanying drawings, in which.

DETAILED DESCRIPTION OF THE PREFERRED EMBODIMENT

In overview, the preferred embodiment of the present invention encompasses a novel tachyarrhythmia detection system and method, which can be used as a primary ECG arrhythmia diagnosis tool or as a backup system to reconfirm arrhythmia detection using conventional techniques. The inventive method provides a means of discriminating between ventricular and supraventricular tachyarrhythmias, or differentiating between ventricular tachycardia and fibrillation, as well as a means of identifying high-frequency noise.

For example, the novel detection algorithm of the present invention can be used to independently quantify the complexity of a cardiac rhythm, which has been preliminarily diagnosed as a tachyarrhythmia by rate algorithm as being either a ventricular or supraventricular tachyarrhythmia, and then further classify the diagnosed ventricular tachyarrhythmia as VT or VF by the calculated complexity measure, at the same time not mis-identify high-frequency noise as VF or VT.

These and other features of the present invention will be more fully understood from the following detailed description, which should be read in light of the accompanying drawings in which corresponding reference numerals refer to corresponding parts. The algorithm is based on the analysis of the non-linear dynamic characteristics of the cardiac intrinsic activity.

Figure 1:
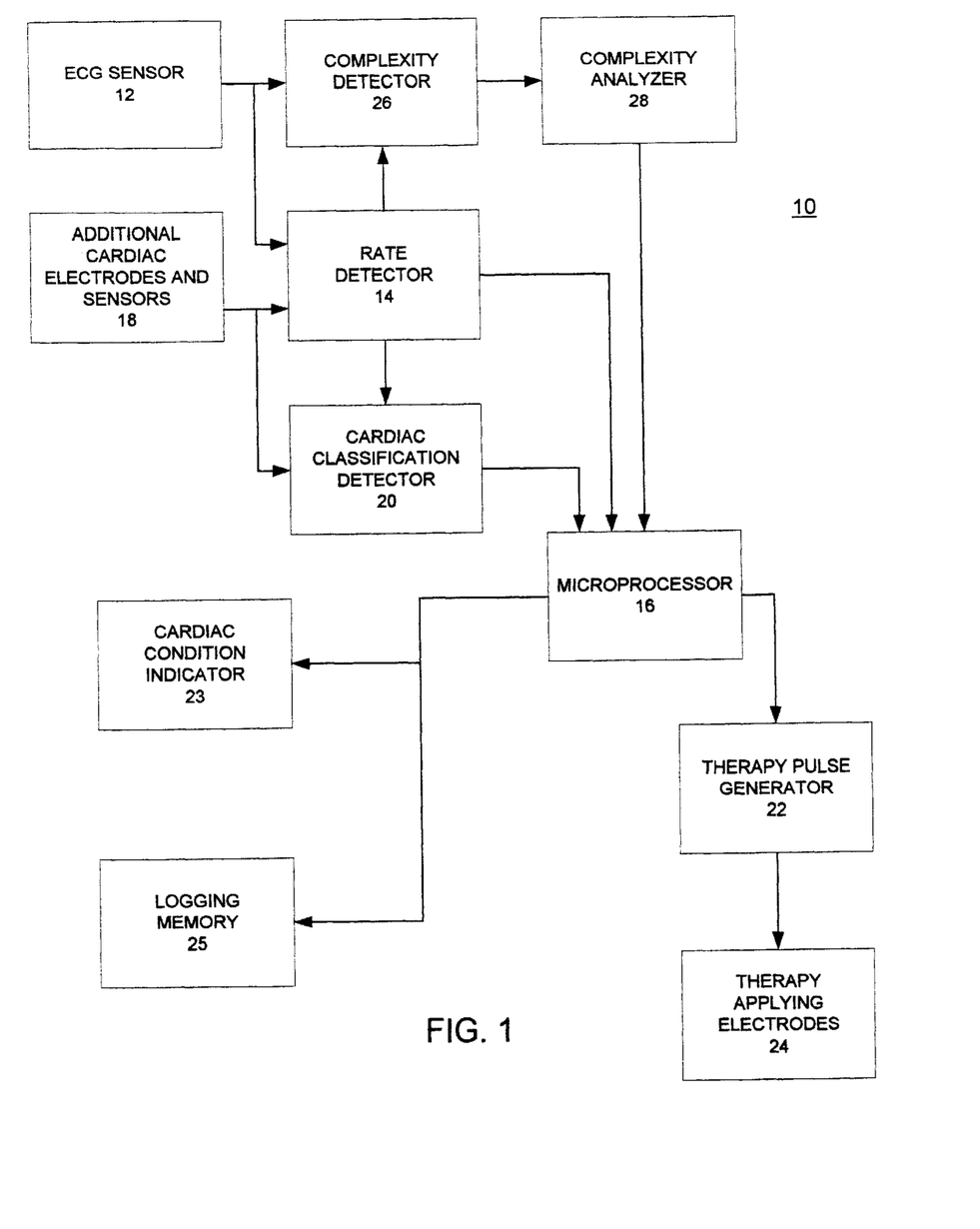
FIG. 1 shows a block diagram of a cardiac device in which the subject invention may be used to differentiate between sinus rhythm and other types of rhythms.

FIG. 1 shows a block diagram of a cardiac device 10 in which the subject invention may be incorporated. The device 10 may be an implantable or external device and it includes an ECG sensor 12 arranged to detect the intrinsic cardiac signals or ECG from the patient and to transmit the same to a rate detector 14. The rate detector determines the current heart rate HR of the patient and transmits it to a microprocessor 16. In some devices, such as, for example, cardiac implants, additional electrodes, and other sensors 18 may be used to detect various intrinsic cardiac activity (such as transthoracic, acceleration or other physiological or activity sensing). The outputs or signals generated by these other devices may also be fed to the rate detector 14. The rate detected by the detector 14 and the signals generated by the other sensors 18 are fed to a conventional cardiac classification detector 20. Detector 20 analyzes the rate and/or other signals from sensors 18 and based on a predetermined algorithm generates an indication of the current state of the heart. This information is presented to the microprocessor 16. The microprocessor analyzes the heart rate of the patient, the cardiac classification detected and other information derived from the signals of sensors 18 and determines an appropriate therapy for the patient (if any).

The microprocessor 16 then activates a therapy pulse generator 22 which generates appropriate pulses. These pulses are applied internally or externally by therapy applying electrodes 24. Some of the electrodes 24 may also be used to sense the ECG or other signals from the patient as well.

In accordance with this invention, the device 10 further includes a complexity detector 26. This detector 26 analyzes the complexity of the intrinsic activity of the heart and generates a parameter CM (complexity measure). This parameter CM is provided to a complexity analyzer 28 which generates an output indicative of the cardiac classification of a patient's heart. This output is provided to the microprocessor 16. The microprocessor uses this output in conjunction with other data it has already calculated or received from the detector 20 to determine the therapy for the patient. Alternatively, this information may be used alone by the detector 20 to determine the proper cardiac classification.

The complexity detector 26 and analyzer 28 could be incorporated into the detector 20, however, it are shown here as discrete elements for the sake of clarity. The detectors 14, 20, 26, and analyzer 28 may also be implemented by software in microprocessor 16.

The device 10 may be a monitor which provides only information about the patient's cardiac condition in which case the pulse generator 22 and therapy applying electrodes 24 are omitted. Instead, a cardiac condition indication 23 is provided by activating external indicia on device 10, by generating an output on a display device, by sending an output signal to a remote display and so on. In addition, the condition indication may be logged in a memory 25 for further analysis and review by a clinician.

Figure 1A:
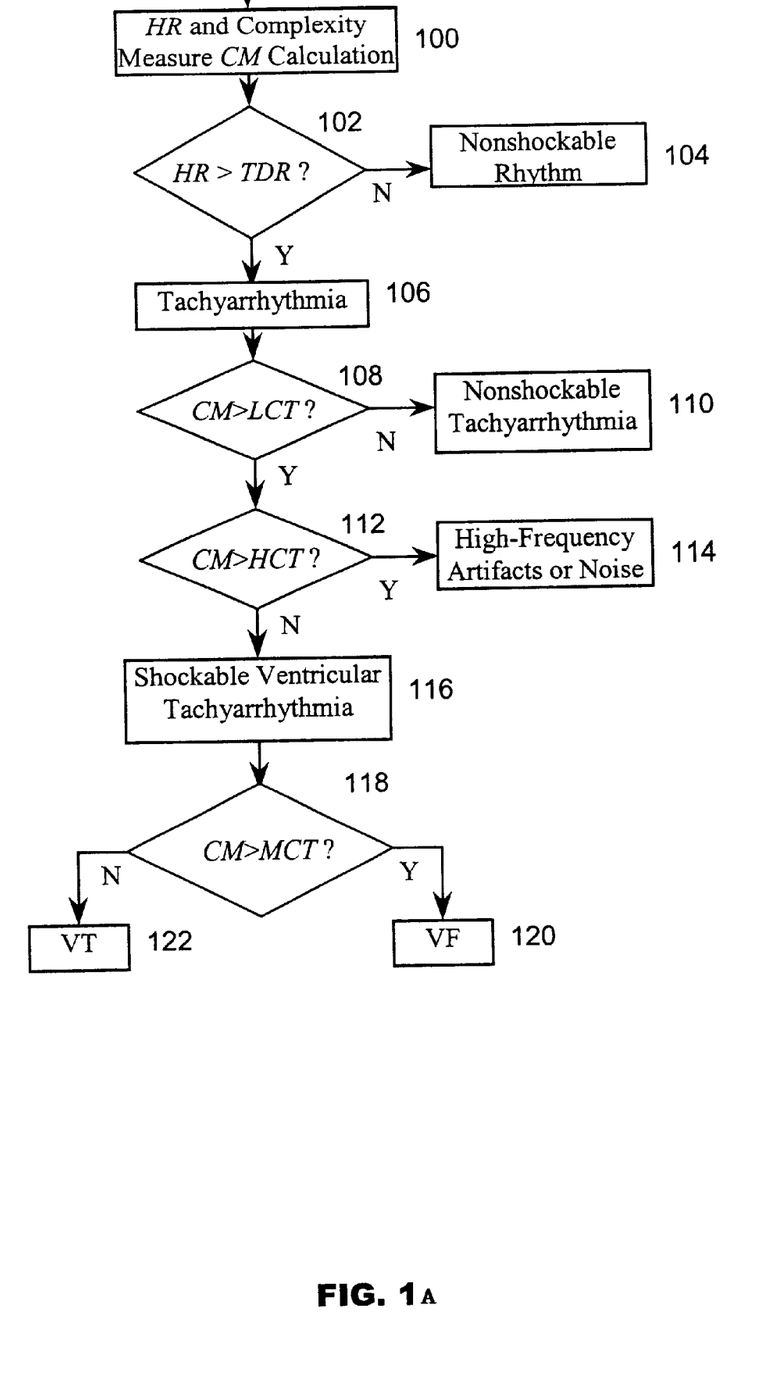
FIG. 1A is a flow chart indicating how a cardiac complexity parameter can be used for discriminating cardiac tachyarrhythmias by complexity measure CM in the device of FIG. 1.

Now referring to FIG. 1A for a general flow chart indicating how a cardiac complexity related parameter can be used for classifying the cardiac condition of the patient. More specifically, in FIG. 1A, a complexity measure parameter (CM) is used to discriminate cardiac tachyarrhythmias. At step 100, heart rate (HR) and complexity measure CM are calculated from ECG signal by the detectors 14 and 26. At the step 102, the current HR is compared to a tachyarrhythmia detection rate (TDR) threshold. TDR my be in the range of 120–240 beats per minute.

If HR is found to be above TDR in step 102, then tachyarrhythmia 106 is indicated. Otherwise, a non-shockable rhythm is indicated in step 104 and no therapy is applied.

If tachyarrhythmia is indicated, then at step 108, the calculated CM is compared to a low complexity threshold (LCT) (e.g. 14, shown by study on database). If CM is not over the LCT, then a non-shockable tachyarrhythmia is indicated in step 110 (including supraventricular tachycardia (SVT), atrial fibrillation and flutter, etc.) and no treatment is provided.

Otherwise, a shockable ventricular tachyarrhythmia, high-frequency artifacts or noises is indicated. At step 112, CM is further compared to a high complexity threshold (HCT) (e.g. 72). If CM>HCT then high-frequency artifacts or noise is identified in step 114 and no therapy is applied. If CM<HCT then shockable ventricular tachyarrhythmia is identified in step 116. In this way, the possible impact of high frequency artifacts or noise on the detection system can be avoided.

In step 118, CM is compared to a mediate complexity threshold (MCT) (e.g. 49) to further differentiate VT and VF from the identified shockable ventricular tachyarrhythmia. If CM is over the MCT, then in step 120, VF is identified and appropriate high-energy defibrillation shocks are applied. Otherwise, VT is indicated and, in step 122, low-energy cardioversion therapy is applied.

Figure 2:
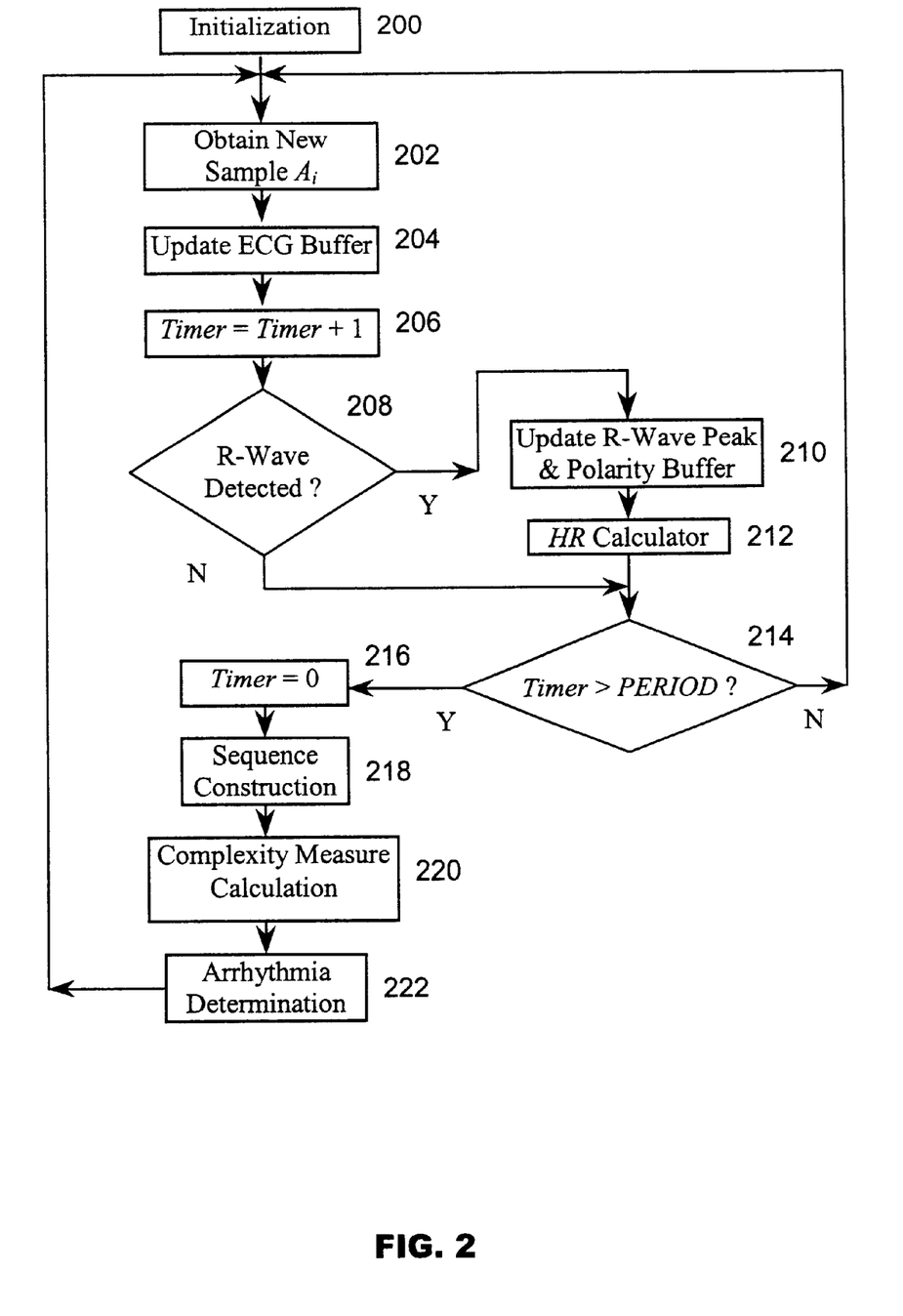
FIG. 2 is a general flow chart for determining the complexity measure CM.
Figure 2A:
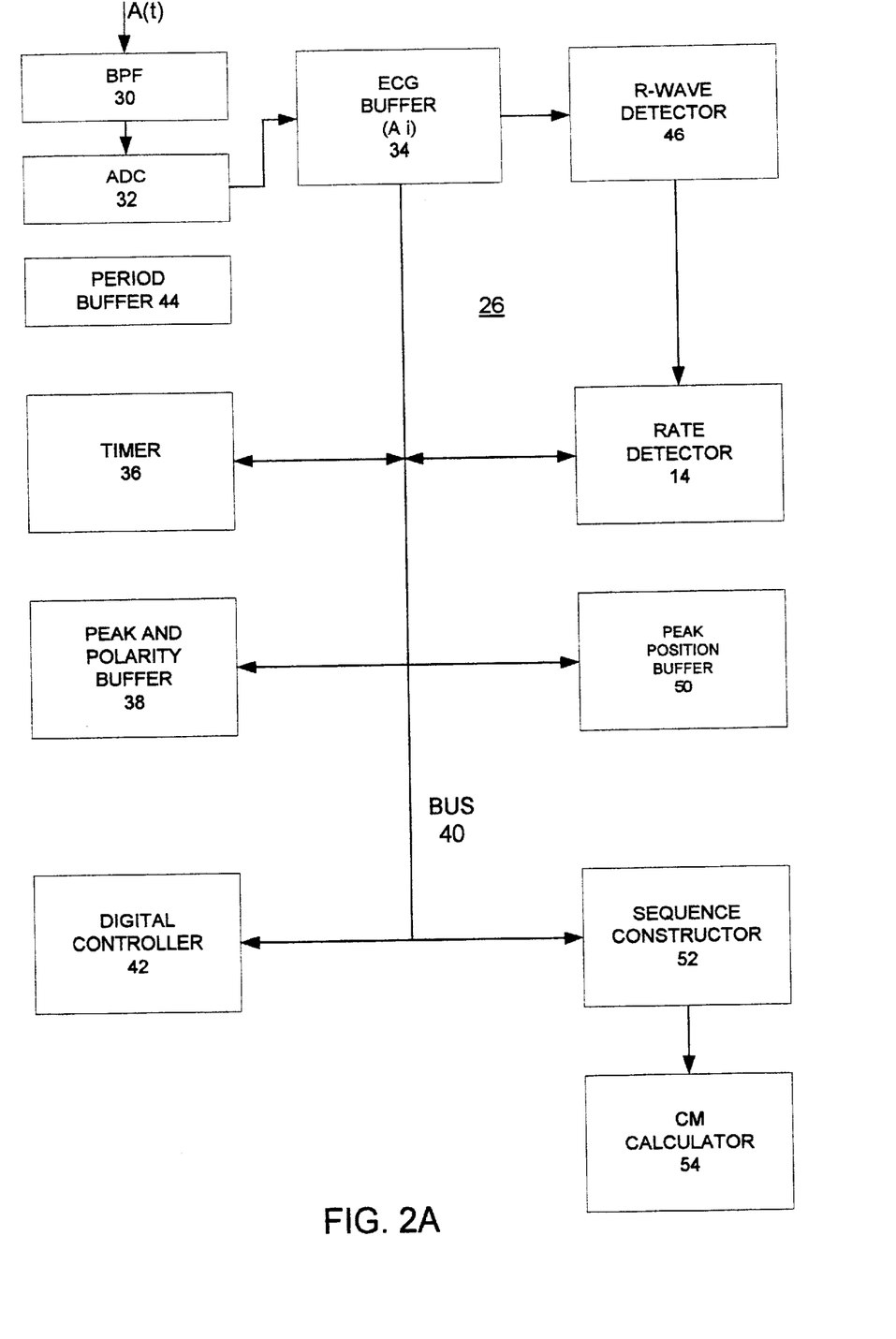
FIG. 2A shows a block diagram for the complexity detector of FIG. 1 that can be used to determine CM as outlined in the flow chart of FIG. 2.

In step 100 in FIG. 1, the determination of HR and CM, is now described in conjunction with FIGS. 2 and 2A. Since in the preferred implementation, the complexity detector 26 requires the current heart rate as well, FIG. 2A shows the elements of the complexity detector 26 and heart rate detector 14.

As seen in FIG. 2A, the signals A(t) from the ECG sensor 12 are filtered by a band-pass filter BPF 30 and then digitized by an ADC 32. The resulting digitized signals are fed into an ECG buffer 34. The circuitry further includes a timer 36, an R-wave peak/polarity buffer 38 and a period buffer 44. Data is transferred from one element of the circuitry to another over a bus 40 in response to commands from a digital controller 42. The circuitry further includes an R-wave detector 46, a peak position buffer 50, a sequence buffer 52, and a CM calculator 54.

The functions of the controller may be performed by the microprocessor 16, however, a separate element is shown herein for the sake of clarity.

In FIG. 2, step 200, the ECG Buffer 34, R-Wave Peak/ polarity, and peak position buffers 38 and 50 and variable Timer 36 are initialized to zero. The constant PERIOD buffer 44 is initialized to twice the sampling rate (i.e. 2 sec long). The constant PERIOD determines the frequency at which the parameter CM is updated. The ECG Buffer 34 is used to store the N latest ECG data samples for estimating the CM parameter. Typically, N may be seven times of sampling rate (i.e. 7 sec. long).

In step 202, a new ECG sample is filtered and digitized. The filter 30 is preferably a passband filter passing signals in the range of 3 to 33 Hz (−3 dB) and being formed of a high- and a low-pass section (not shown). The low-pass section also serves as an anti-aliasing filter and smooths transitions of the ECG so that the peaks may easily be identified. The high-pass section serves to remove any baseline wander from the signal, so that a separate DC removal stage is not required. ADC 32 is preferably a 12-bit ADC. $A_i$ is zero for 2048 ADC units ($ADC_{zero}$), for 4095 ADC units it is +5 mV, and for 0 ADC unit is −5 mV for a bipolar ECG signal. The baseline ($ADC_{zero}$) is subtracted from $A_i$ by the ADC, therefore, if $A_i$ is above the baseline, its value is positive, or otherwise, it is negative.

In step 204, the ECG buffer 34 is updated by shifting out the oldest data sample and shifting in the newest one $A_i$. In this manner the ECG buffer 34 always contains the latest N ECG data samples $\{A_1, A_2, A_3, \ldots, A_j, A_{j+i}, \ldots, A_{N-1}, A_N\}$. In step 206, the timer 36 is augmented by one.

In step 208, the R-wave detector 46 checks the data in buffer 34 to determine if an R-wave is present or not. The R-wave detection can be implemented by rate detector 14 in various well-known schemes. If R-wave is not detected, step 214 is implemented to check the timer 36, as discussed below. Otherwise, the R-Wave Peak/ polarity and peak position buffers 38 and 50 are updated by storing in buffer 38 the size and polarity of the peaks and storing the positions of the peaks in buffer 50 for the newly detected R-Wave in step 210. Next, the HR detector 14 determines the current heart rate (HR) in step 212 by averaging the R-R intervals of the last seven seconds. The R-R wave intervals which can be obtained from the R-Wave Peak, position and polarity buffers. Thus, the heart rate HR is calculated from the latest N ECG data samples obtained during the last 7 sec. Of course, the rate detector 14 may use other criteria for determining the current heart rate HR as well.

In step 214, if the content of the timer 36 has not exceeded the PERIOD parameter, the program continues acquiring the next new ECG data $A_i$ by returning to step 202 and processing the data. When the contents of the Timer exceed the PERIOD then in step 216 the Timer 36 is reset.

In step 218, the sequence constructor 52 transforms the ECG data stored in the ECG buffer 34 into a binary sequence S with length N. Details for performing this transformation are provided below. The sequence S is designed to preserve all the non-linear dynamic characteristics of the ECG signal in buffer 34.

The binary sequence S is then provided to the CM calculator 54 in step 220. The CM calculator 54 then processes the sequence S and generates the parameter CM as described more fully below. Next, in step 222, the CM parameter is transmitted to the complexity analyzer 28 (FIG. 1) where it is analyzed and an arrhythmia determination is made in step 222 (as outlined above and in FIG. 1A) regarding the type of current cardiac episode. Then the program starts next operation cycle by returning to step 202. In this way, every interval of PERIOD (i.e. 2 sec.), one value for parameter CM is calculated and the type of rhythm is determined. Since the number of ECG data used to calculate the CM is N (i.e. 7 sec.), there is an overlap (N-PERIOD, i.e. 5 sec.) between the ECG data segments for calculating current CM and previous CM.

Figure 3:
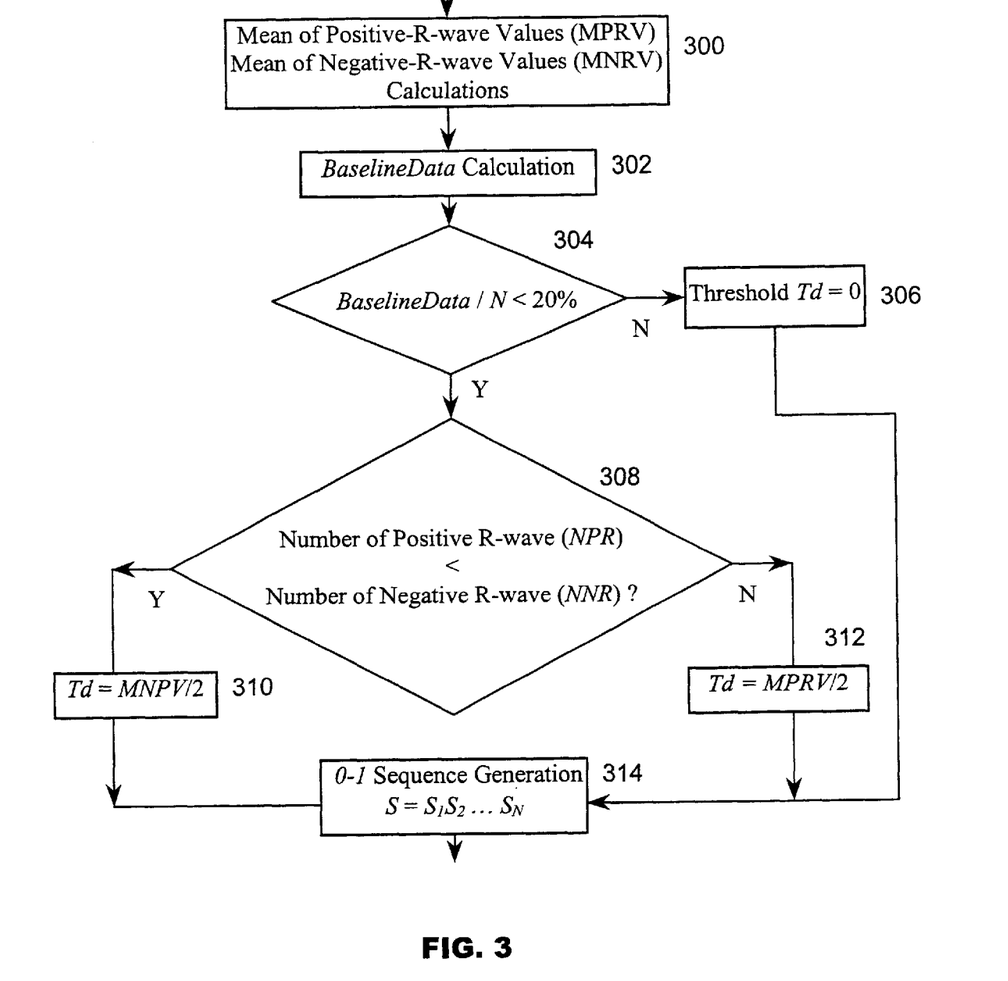
FIG. 3 is a flow chart for transforming an ECG data series into a corresponding binary sequence S.
Figure 3A:
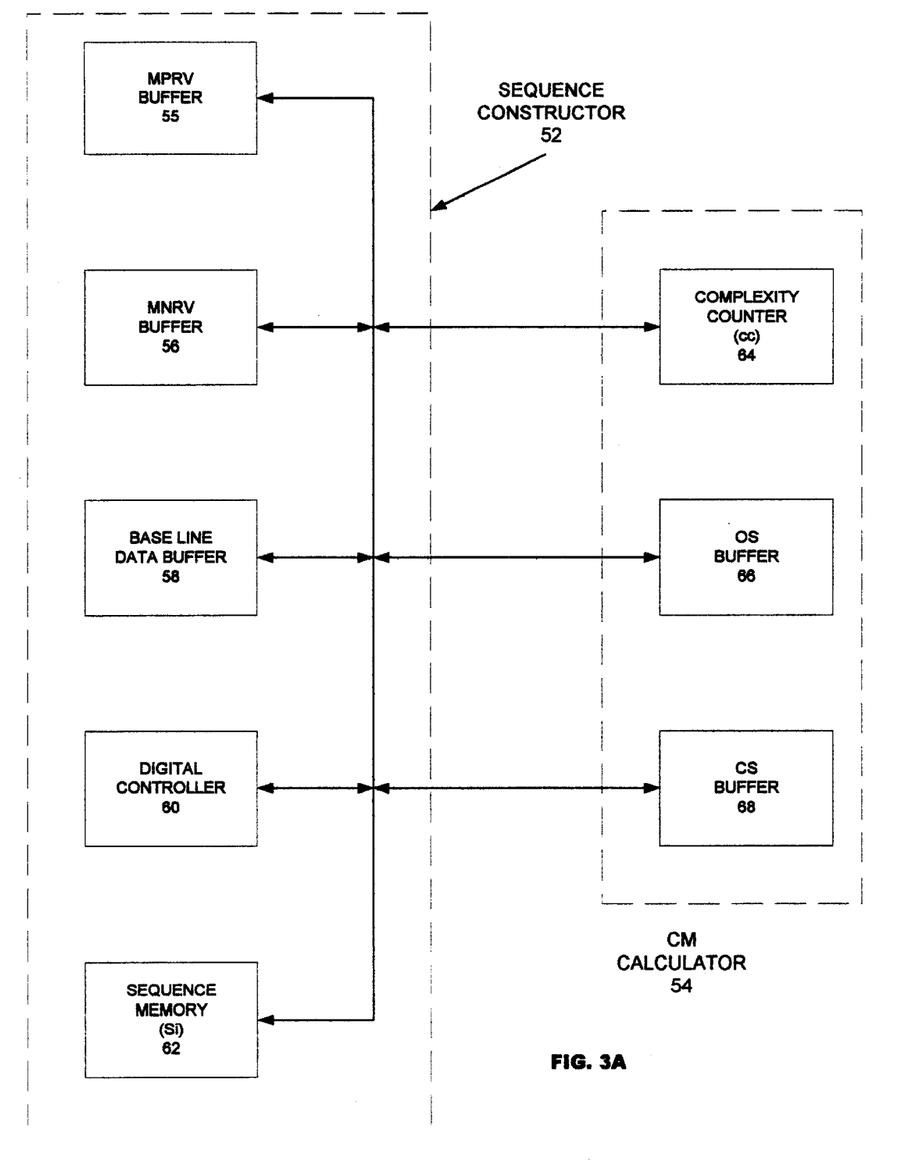
FIG. 3A shows a block diagram for a sequence constructor and CM calculator for performing the transformation of FIG. 3.

FIG. 3 further illustrates the operation of the sequence constructor 52 while FIG. 3A shows details of the sequence constructor 52. The sequence constructor 52 includes an MRPV buffer 55, an MNRV buffer 56 a baseline data buffer 58, and a digital processor 60. The functions of the digital processor 60 can be performed by processor 16 of FIG. 1, however, a separate processor is shown herein for the sake of clarity.

The buffers 55 and 56 are used to store mean of the positive peaks of the R-waves (MPRV) and the mean of the negative peaks of the R-waves (MNRV) respectively of the peaks stored in peak/polarity buffer 38. If there is no negative R-wave stored, then the MNRV buffer 56 is set to −33% of the MPRV in buffer 55. If there is no positive R-wave stored then MPRV is set to −33% of the MNRV in buffer 56. The baseline data buffer 58 is used to hold the number of data points from the set of the ECG buffer 34 which define a baseline for the R-waves. The processor 60 is used to manipulate the data in these buffers as described below. The results of these manipulation are stored as a coefficient cc in a complexity count buffer 64.

In step 300, the MPRV and MNRV parameters are determined and stored in the respective buffers 55, 56. Next the number of data samples in the ECG buffer 34 falling in a predetermined range (for example between 10% of MNRV and 10% of MPRV), are determined and stored in the BaselineData buffer 58 (step 302).

Next, in step 304 the ratio BaselineData/N is determined. If this ratio is larger than 20%, then a Threshold Td is set as 0 in step 306 and goes to step 314.

If the ratio is larger than 20%, then the number of positive R-wave (NPR) is compared to the number of negative R-wave (NNR) in step 308. If NPR is smaller than NNR, then Td is set to MNPV/2 in step 310, otherwise, Td set to MPRV/2 in step 312.

Finally, in step 314, the ECG data $\{A_1, A_2, A_3, \ldots, A_j, A_{j+1}, \ldots, A_{N-1}, A_N\}$ is transformed into a binary sequence $S = S_1 S_2 \ldots S_N$ by using the following criteria:

If $A_j > Td$, then $S_j = 1$, otherwise, $S_j = 0$ for all $j = 1, 2, \ldots, N$.

In this manner the sequence S is thus constructed in a manner so as to preserve the spatio-temporal patterns characteristic of the ventricular activities in the patient's heart in a compact and manageable format. Series S is stored in sequence buffer 62.

Figure 4:
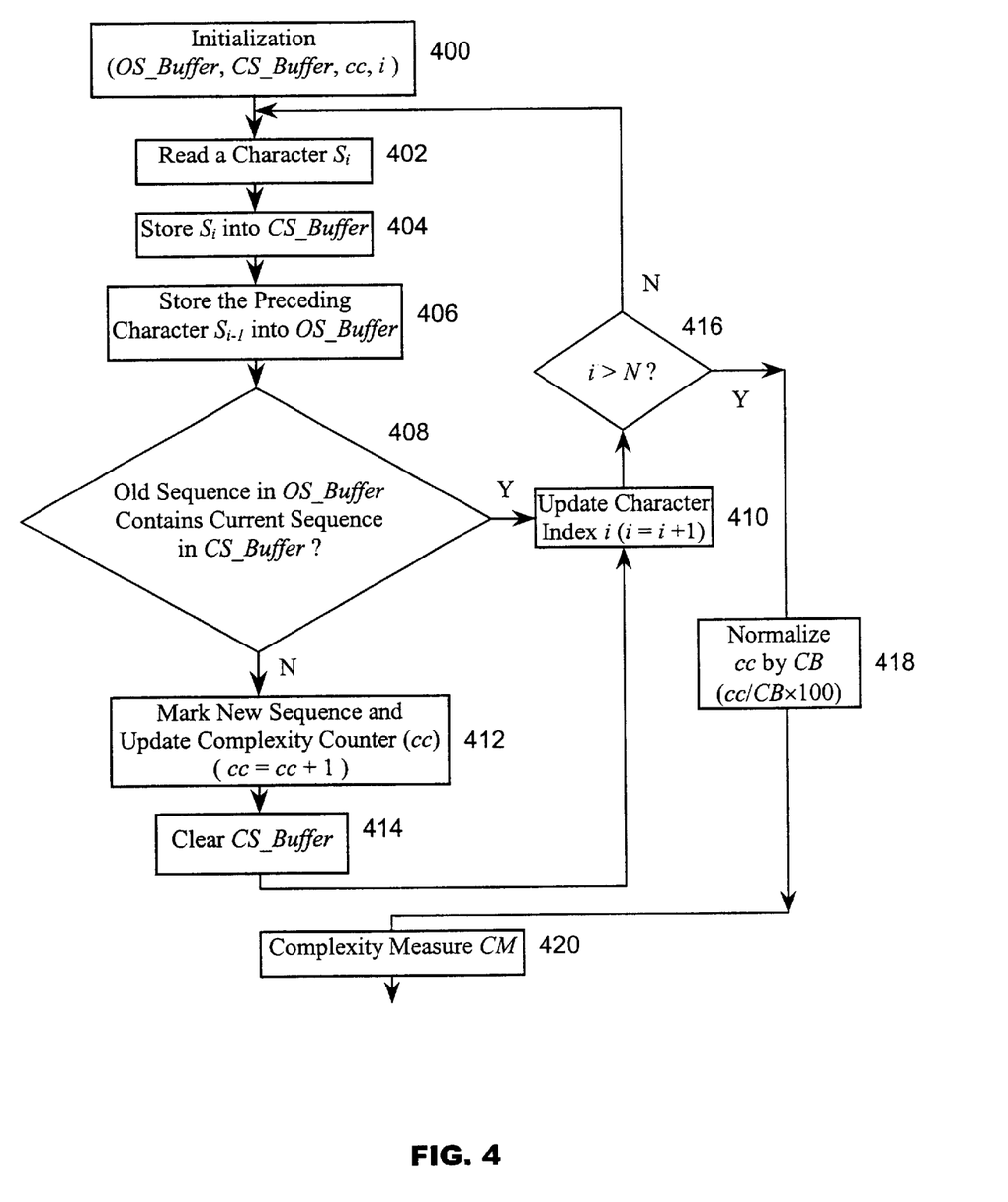
FIG. 4 is a detailed flow chart illustrating how to determine the complexity measure CM from the binary sequence S using the sequence constructor and CM calculator of FIG. 3A.

The algorithm used by the CM calculator 54 (FIG. 2A) in step 220 is depicted in more detail FIG. 4 while details of the CM calculator are also shown in FIG. 3A. As seen in FIG. 3A, the CM calculator 54 includes an old sequence (OS) buffer 66, a current sequence (CS) buffer 68 and the complexity counter 64.

Briefly speaking, the binary sequence $S = S_1 S_2 \ldots S_N$ is scanned from left to right and character by character, and the complexity counter 64 is increased by one every time a new sub-sequence of consecutive binary characters is encountered during the scanning process. When the whole sequence S has been scanned, the process for calculating the complexity measurement has been completed and the contents of the complexity counter is fed to the complexity analyzer 28 as parameter CM.

Getting back to FIG. 4, in step 400 the CM calculator is initialized by setting the complexity counter 64 to 0, setting the character index (i) to 1, and clearing the old sequence buffer 66 and the current sequence buffer 68. In step 402 a character $S_i$ is read from the binary sequence $S=S_1 S_2 \ldots S_N$, starting from the first character $S_1$. In step 404, the character $S_i$ is stored in the current sequence buffer 68. In step 406 the character $S_{i-1}$, preceding $S_i$, is stored in the old sequence buffer 66. If i=1 (i.e. for the first character $S_1$), $S_{i-1}$, (i.e. $S_0$) is null.

In step 408, the current sequence located in the CS_Buffer 68 is compared to the old sequence located in the OS_Buffer 66. If the old sequence contains the current sequence (i.e. the current sequence can be copied from the old one), then the current sequence is not a new sequence and step 410 just updates the character index i (i=i+1) for reading next character. If the old sequence does not contain the current sequence at step 408, then the current sequence is a new one, and in step 412 the new sequence is marked and the complexity counter 64 is updated (cc=cc+1).

In step 414, the CS_Buffer 68 is cleared and then the process continues with step 410 to update the character index i.

In step 416, the current index i is compared to N (the length of the binary sequence S). If i is not larger than N, then a new character $S_i$ is read in step 402.

If i is larger than N (i.e. out of the length of the sequence S), then the scanning process is terminated. In step 418, the count in complexity counter 64 is normalized by the processor 60 using the peak or boundary value CB. Normalizing may comprise of normalizing the cc by complexity boundary value (CB): CM=cc/CB*100, where CB=91 (i.e. $N/\log_2(N)=896/\log_2(896)=91$ for 7 sec. ECG data series under the sampling rate 128 Hz).

Finally, in step 420, the processor 60 outputs the calculated complexity measure CM, said parameter being in the range of 0 to 100. As can be seen in the cc calculation, the key part of the algorithm is very simple, just use two simple operations: character comparison and number accumulation. Therefore, it is very easy to implement by software or hardware (either in digital electronics, or with low computational overhead on a microprocessor).

As demonstrated above, the novel tachyarrhythmia detection method disclosed in the present invention has following advantages:

1) It is computationally simple, easy to implement by software or hardware. All the processing is done with integer arithmetics without requiring excessive computing power, thus reducing the hardware requirement. Hence, the CM can be easily implemented in an AED or ICD.

2) It provides multiple functions: Not only discriminating shockable VT and VF from non-shockable SVT (the main cause of false therapy), but also differentiating VT and VF, thereby providing multi-therapies for different arrhythmias. In addition, high-frequency noise can also be identified from the arrhythmias to avoid the interference of the noise on the arrhythmia detection. All these features are particularly useful in AEDs and ICDs.

3) It is rapid and robust: By checking the CM every PERIOD (i.e. 2 sec.), it can closely track the change of the ECG signal and identify any possible VF or VT for timely and suitable electrical therapy, and at the same time avoid unnecessary shock therapy for SVT and any possible interference of the high-frequency noise. Moreover, the threshold selection Td to immunizes the system from some low frequency artifacts or wander.

Although the present invention has been described in detail hereinabove, it should be clearly understood that many alternatives to the embodiments and/or modifications of the basic inventive concepts taught herein and which may appear as such to those skilled in the art, will still fall within the spirit and scope of the present invention, as defined in the claims. For examples, at step 218, using other kinds of Threshold Td determination method modified from FIG. 3, such as taking a fraction of the largest R peak absolute value as Td, or fraction of the average of all the R peak absolute value as Td; or just triggering the binary Sequence Construction step 218 and the Complexity Measure CM Calculation step 220 only if the estimated HR by step 210 exceeding a pre-set threshold TDR (i.e. tachyarrhythmia occurs) by moving the step 102 to the position between 216 and 218, or adding some other commonly used measures into the algorithm for combination use in tachyarrhythmia determination.

The present invention will be further understood according to the following description of the specific examples.

EXAMPLE 1

Figure 5:
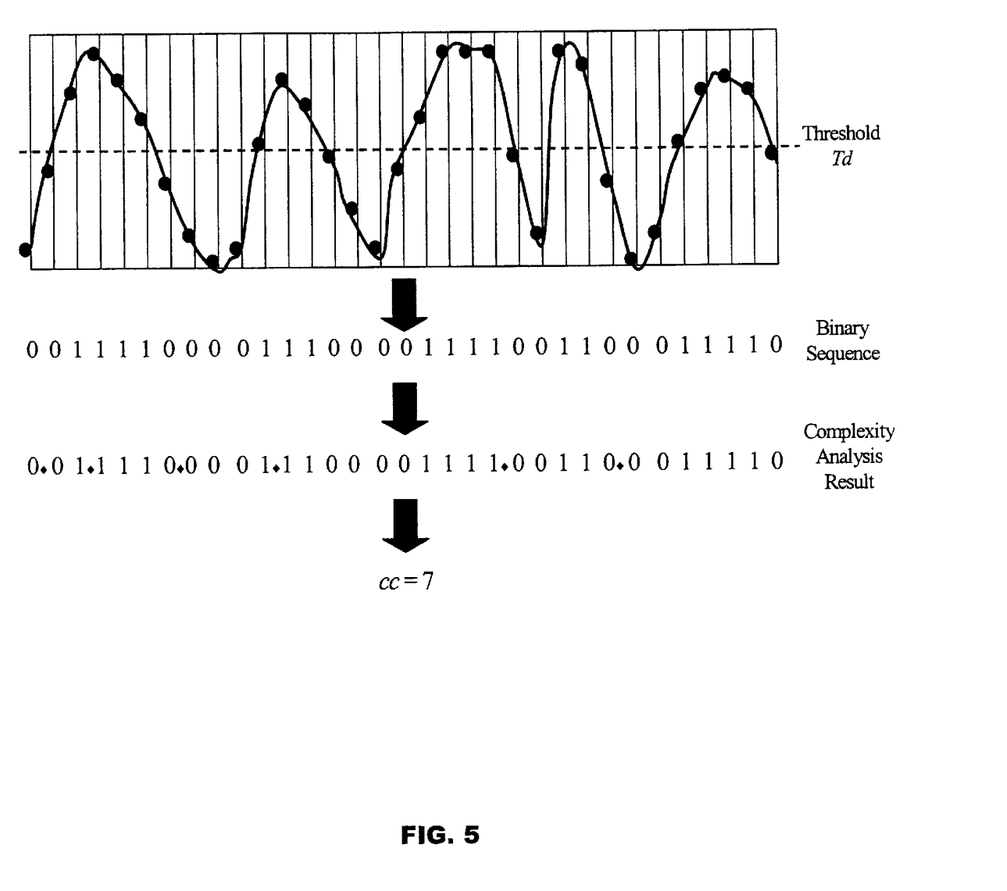
FIG. 5 is an exemplary illustration showing how to transform an ECG data series into a binary sequence by threshold method and the result by complexity analysis on the binary sequence S.

First the invention is illustrated in conjunction with relatively simple waveform to illustrate how the CM parameter is obtained. FIG. 5 shows an analog ECG waveform represented by a solid curve. After filtering, the signal is digitized at every sampling interval of the grid. The solid dots "•" on the ECG waveform denote the digital data samples collected from the ECG signal, i.e., each dot represents one of the values $A_i$. The horizontal dashed line, across the figure, denotes the Threshold Td. Using Td, the ECG data series $A_i$ is transformed into the sequence S. In this sequence S, if the corresponding dot "•" is above the Td, then the character $S_i$ corresponding to the "•" is "1", otherwise, it is "0". The resulting sequence S is shown in FIG. 5 below the ECG curve as the binary sequence S=001111000011100001111001100011110 (length N=33), as described in FIGS. 2 and 3.

EXAMPLE 2

From this sequence S, the number of different sub-sequences (as determined by the complex counter 64 in FIG. 3A and described in FIG. 4) contained in S are calculated by complexity analysis as follows.

First, let P and V denote, respectively, two mutually exclusive sub-sequences of the sequence S, and PV be the concatenation of P and V, while string PVd is derived from PV after its last character ("0" or "1") is deleted (d defines the operation in which the last character of PV is deleted). Moreover, Let symbol "♦" the end of each different sub-sequence.

(1) First character (i.e., in this case 0) is always a new one. Therefore the first sub-sequence is →0♦.

(2) The second character of S is 0 and this is identical to the first sub-sequence. In this case P=0, the new sub-sequence V=0; PV=00 and PVd=0. Therefore, PVd contains V, so V is not a new sub-sequence →0♦0.

(3) The third character of S is 1. The previous sub-sequence (before "♦") is 0 and therefore P=0, the new sub-sequence V=01; PV=001, PVd=00. Therefore, PVd does not contain V, so V is a new sub-sequence →0♦01♦.

(4) The next character of S is 1. The previous sub-sequence (before the second "♦")is P=001. The new sub-sequence V=1, PV=0011, PVd=001. Therefore, PVd contains V, so V is not a new sub-sequence →0♦01♦1.

(5) The fifth character is a 1. The previous sub-sequence (before the second"♦") is P=001, the new sub-sequence V=11, PV=00111, PVd=0011. PVd contains V, so V is not a new sub-sequence →0♦01♦11.

(6) The sixth character is a 1, therefore, the previous sub-sequence (before the second "♦") P=001, the new sub-sequence V=111, PV=001111, PVd=00111. PVd contains V, so V is not a new sub-sequence →0♦01♦111.

(7) The seventh character is a 0. The previous sub-sequence (before the second "♦") P=001. The new sub-sequence V=1110, PV=0011110, PVd=001111. PVd does not contain V, so V is a new sub-sequence →0♦01♦1110♦.

(8) The eight character is a 0. The previous sub-sequence (before the third"♦") P=0011110. The new sub-sequence V=0; PV=00111100, PVd=0011110. PVd contains V, so V is not a new sub-sequence →0♦01♦1110♦0.

(9) The ninth character is a 0. The previous sub-sequence (before the third"♦") P=0011110. The new sub-sequence V=00, PV=001111000, PVd=00111100. Therefore, PVd contains V, so V is not a new sub-sequence →0♦01♦1110♦00.

(10) The tenth character is a 0. The previous sub-sequence (before the third"♦") P=0011110. The new sub-sequence V=000, PV=0011110000, PVd=001111000. PVd contains V, so V is not a new sub-sequence →0♦01♦1110♦000.

(11) The eleventh character is a 1. The previous sub-sequence (before the third "♦")P=0011110. The new sub-sequence V=0001, PV=00111100001, PVd=0011110000. Therefore, PVd does not contain V, so V is a new sub-sequence →0♦01♦1110♦0001♦.

(12) The twelfth character is a 1. The previous sub-sequence (before the fourth "♦")P=00111100001. The new sub-sequence V=1, PV=001111000011, PVd=00111100001. PVd contains V, so V is not a new sub-sequence →0♦01♦1110♦0001♦1.

Using this process the series is scanned and segmented as follows:
→S=0♦01♦1110♦0001♦1100001111♦00110♦0011110.

The number of sub-sequence (i.e. distinct patterns) divided by "♦" in S is 7 and this is the number stored in the complexity counter 64. The corresponding complexity measure CM can be further obtained by normalizing cc.

Figure 6A:
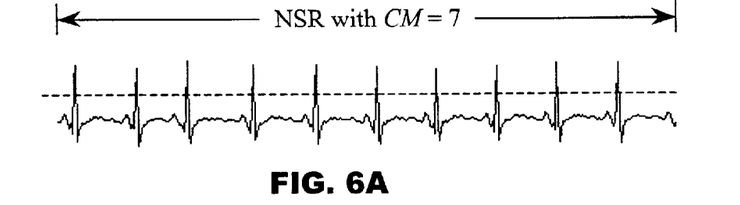
FIGS. 6A–6E illustrate some exemplary ECG rhythms and high-frequency noise with their corresponding complexity measure CM's (dashed line meaning the position of the threshold).
Figure 6B:
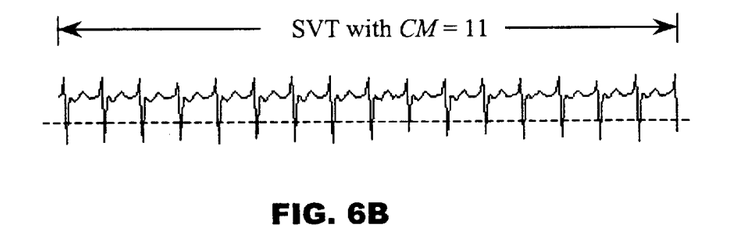
Figure 6C:
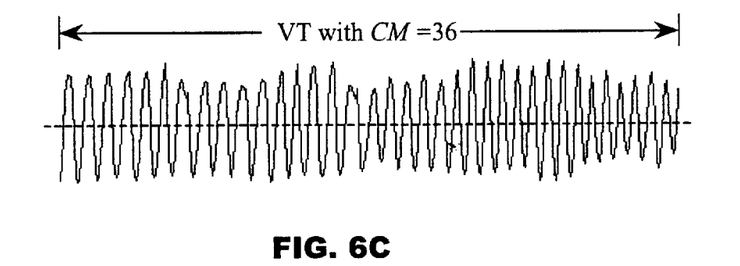
Figure 6D:
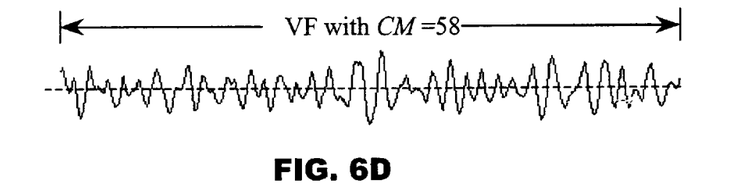
Figure 6E:
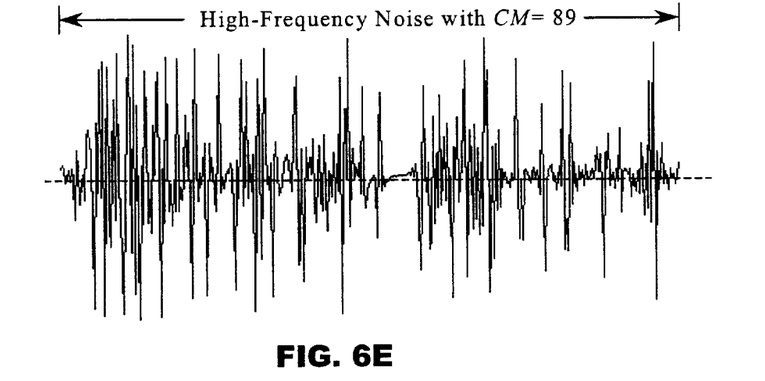

The waveforms of some typical cardiac rhythms and high-frequency noise along with the corresponding complexity measure CM are illustrated in FIGS. 6A–6E. The dashed line denotes the corresponding threshold Td, used to transform the ECG data series into binary sequence S. An example of a normal sinus rhythm (NSR) with CM=7 is shown in FIG. 6A. An example of SVT with CM=11 shown in FIG. 6B, an example of VT with CM=36 in FIG. 6C, an example of VF with CM=58 in FIG. 6D, and an example of high-frequency noise with CM=89 in FIG. 6E. These cases differ from each other because their inherently different underlying nonlinear dynamics and corresponding complex-ity. This difference is reflected quantitatively characterized by the value of CM.

ECG signals as well as the methods of acquiring them are well-known in the art. As used herein, an ECG refers to a body surface electrocardiogram as example, but other forms of electrocardiogram would also work with the methods disclosed herein, and are within the scope and spirit of the invention. For example, an epicardial ECG, an endocardial ECG, or other related signal measured in or near the heart and indicative of its intrinsic dynamic activity. Moreover, the signal which is manipulated may be a voltage signal, a current signal, or another related electromagnetic values.

Moreover, instead of the ECG, other signals may be used to sense ply the disclosed complexity measure concept and preferred algorithms to other kinds of physiological signals, such as R-R interval series extracted from cardiac electrograms, blood pressure, vasomotor tone, electromyography(EMG), electrodermography, electroneuography, electro-oculography(EOG), electroretinography(ERG), electronystagmography (ENG), video-oculography (VOG), infrared oculography (IROG), auditory evoked potentials (AEP), visual-evoked potentials (VEP), all kinds of Doppler signal, etc.

Returning to FIGS. 1A and 1, once the CM is determined, the microprocessor 16 may make use of this parameter in a number of different modes. In the simplest mode, the microprocessor uses the CM parameter to determine the condition of the patient and then applies appropriate therapy, in accordance with the flow chart of FIG. 1A. In a second mode, the device 10 includes a second detector such as classification 20 which performs an independent determination of the condition of the patient's heart and/or the type of therapy that is most suitable for the patient using conventional techniques well known in the art, such as cardiac rate, ECG morphology, transthorasic impedance, etc. The microprocessor may then be programmed to use the determination of detector 20 as the primary decision criteria and use the CM parameter as a confirmation criteria to insure that the patient does not get unnecessary shocks. More specifically, if detector 20 indicates ventricular fibrillation, the microprocessor checks the CM parameter to confirm that VF is detected by the latter parameter as well before administering defibrillation shocks. Confirmation may be required for other types of therapies as well.

Of course, the microprocessor may use the CM parameter as the primary cardiac indicia, and use the output of the conventional detector 20 as a confirmation criteria.

In other modes of operation the outputs of analyzer 28 and detector 20 may be weighted using some predetermined criteria and the combined result may be used as a criteria for applying therapy.

Numerous modifications may be made to this invention without departing from its scope as defined in the appended claims.

We claim:

1. A system for detecting cardiac arrhythmia comprising:
    a sensor that senses an intrinsic signal indicative of cardiac activity;
    a signal processor receiving said intrinsic signal and transforming said intrinsic signal into a sequence S indicative of non-linear characteristics of said cardiac activity;
    a calculator arranged to operate on said signal S to determine a complexity measure CM indicative of the complexity of a dynamic behavior of said cardiac activity; and
    a complexity analyzer that analyzes said complexity measure CM to derive a current condition of the heart and generates a corresponding output, wherein said complexity analyzer includes a first comparator that compares said complexity measure CM to a first threshold TDR to detect a non-shockable rhythm and a second comparator that compares said complexity measure CM to a second threshold HCT to detect a high frequency noise;

said complexity analyzer being adapted to distinguish between cardiac classifications of the heart including a nonshockable rhythm, ventricular tachycardia and ventricular fibrillation.

2. The system of claim 1 wherein said signal processor includes a comparator that compares magnitudes of said intrinsic signal to a threshold Td and generates said sequence S based on said comparison.

3. The system of claim 2 further comprising a pattern recognition element arranged to receive said sequence S and to recognize repetitive sub-sequences in said sequence S.

4. The system of claim 3 wherein said calculator further comprises a counter arranged to count said sub-sequences, wherein each counted sub-sequence is unique in that said sub-sequence does not contain any of the previous sub-sequences, said counter generating a count that is used by said calculator in determining said complexity measure CM.

5. The system of claim 4 wherein said calculator further includes a normalizer adapted to normalize said count to be used by said calculator in generating said complexity measure CM.

6. The system of 5 claim wherein said normalizer is adapted to normalize said count to limit said complexity measure to a predetermined range.

7. The system of claim 1 wherein said sensor is arranged to sense a plurality of ECG signals over a predetermined time period, said ECG signals including a plurality of peaks.

8. The system of claim 7 further comprising a buffer that stores a magnitude of said peaks and a threshold calculator adapted to determine a threshold Td based on said magnitudes.

9. The system of claim 8 wherein said buffer stores peak magnitudes of positive and negative peaks, and further comprising a second buffer adapted to store a mean value related to said peaks, and a threshold Td being related to said mean value.

10. The system of claim 1 further comprising a third comparator that compares said complexity measure CM to a third threshold LCT to detect a non-shockable tachycardia.

11. The system of claim 10 further comprising a fourth comparator that compares said complexity measure CM to a fourth threshold MCT to differentiate between ventricular tachycardia and ventricular fibrillation.

12. The system of claim 1 wherein said complexity analyzer determines a patient's heart condition by determining whether said complexity measure is within a predetermined range.

13. The system of claim 1 further comprising a heart rate detector coupled to said sensor and arranged to detect a heart rate HR for the patient based on said intrinsic signal.

14. The system of claim 3 further comprising a timer and wherein said heart rate detector detects a current heart rate of the patient based on time-dependent measurements determined by said timer.

15. The system of claim 1 wherein the cardiac activity exhibits non-linear dynamic behavior and wherein said wherein said calculator is adapted to generate said complexity measure CM as a parameter indicative of said non-linear dynamic behaviour.

16. A cardiac device incorporating the system of claim 1 and adapted to provide one of an indication of a patient's cardiac condition and antiarrhythmia therapy based on said complexity measure.

17. The cardiac device of claim 16 wherein said device includes therapy means to provide antitachycardia therapy based on said output.

18. The cardiac device of claim 16 wherein said device includes therapy means arranged to provide defibrillation therapy based on said output.

19. The cardiac device of claim 16 wherein said device includes therapy means arranged to provide cardioversion therapy based on said output.

20. The cardiac device of claim 16 wherein said device includes means to provide antibradicardia therapy based on said output.

21. The cardiac device of claim 16 wherein said device includes an implantable housing and wherein said system is disposed in said implantable housing.

22. The cardiac device of claim 16 wherein said device includes an external device and wherein said system is disposed within said external device.

23. A device incorporating the system of claim 1 further comprising an indicating means adapted to provide an indication of a patient's condition based on said complexity measure CM.

24. A device for applying antitachyarrhythmic therapy to a patient's heart comprising:

a sensor that senses an intrinsic signal indicative of cardiac activity of the patient, said cardiac activity exhibiting a non-linear dynamic behavior;

a complexity calculator adapted to determine a complexity measure indicative of the complexity of said intrinsic signal;

a complexity analyzer adapted to analyze the condition of the heart by determining if said complexity measure CM is characteristic of treatable and non-shockable tachyarrhythmia, wherein said complexity analyzer includes a first comparator that compares said complexity measure CM to a first threshold TDR to detect a non-shockable tachyarrhythmia and a second comparator that compares said complexity measure CM to a second threshold HCT to detect a high frequency noise;

a conventional cardiac detector adapted to generate a cardiac signal using conventional techniques; and a controller adapted to receive said CM and said cardiac signal and to generate commands defining cardiac therapy based on both said CM and said cardiac signal if said CM is in a range characteristic of treatable tachyarrhythmia.

25. The device of claim 24 wherein said controller is adapted to generate defibrillation commands defining defibrillation shocks, said defibrillation commands being generated only if said CM parameter is indicative of a VF condition in the patient's heart.

26. The system of claim 24 further comprising a third comparator that compares said complexity measure CM to a third threshold LCT to detect a non-shockable tachycardia.

27. The system of claim 26 further comprising a fourth comparator that compares said complexity measure CM to a fourth threshold MCT to differentiate between ventricular tachycardia and ventricular fibrillation.

28. The system of claim 24 further comprising a heart rate detector coupled to said sensor and arranged to detect a heart rate HR for the patient based on said intrinsic signal.

29. The system of claim 28 further comprising a timer and wherein said detector detects a current heart rate of the patient based on time-dependent measurements by said timer of said intrinsic signal.

30. The system of claim 24 wherein the cardiac activity exhibits non-linear dynamic behavior and wherein said wherein said calculator is adapted to generate said complexity measure CM as a parameter indicative of said non-linear dynamic behaviour.

31. The system of claim 24 further comprising a transforming element adapted to transform said intrinsic signal into a signal S indicative of non-linear dynamic characteristics of the heart, wherein said complexity analyzer derives said complexity measure from said signal S.

* * * * *